(12) United States Patent
Rominger et al.

(10) Patent No.: US 10,918,405 B2
(45) Date of Patent: Feb. 16, 2021

(54) SURGICAL INSTRUMENT

(71) Applicant: Karl Storz SE & Co. KG, Tuttlingen (DE)

(72) Inventors: Markus Rominger, Seitingen-Oberflacht (DE); Karl-Heinz Haunschild, Tuttlingen (DE); Jochen Schmidberger, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 262 days.

(21) Appl. No.: 16/043,720

(22) Filed: Jul. 24, 2018

(65) Prior Publication Data
US 2019/0029704 A1 Jan. 31, 2019

(30) Foreign Application Priority Data
Jul. 26, 2017 (DE) ..................... 10 2017 116 935.0

(51) Int. Cl.
*A61B 17/29* (2006.01)
*A61B 90/00* (2016.01)
(Continued)

(52) U.S. Cl.
CPC .......... *A61B 17/29* (2013.01); *A61B 17/1611* (2013.01); *A61B 90/08* (2016.02);
(Continued)

(58) Field of Classification Search
CPC ...... A61B 17/1604–1611; A61B 17/28; A61B 2017/2946; A61B 2017/2919;
(Continued)

(56) References Cited

U.S. PATENT DOCUMENTS 5,961,531 A * 10/1999 Weber ................ A61B 17/1611 604/22
6,685,710 B2 * 2/2004 Agbodoe ........... A61B 17/1611 606/170

(Continued)

FOREIGN PATENT DOCUMENTS

DE 102006012754 A1 9/2007
DE 202009017555 U1 4/2010

OTHER PUBLICATIONS

Search Report for DE 10 2017 116 935.0, dated May 9, 2018 (in German with attached partial English translation) (14 pp.).

*Primary Examiner* — Katrina M Stransky
*Assistant Examiner* — Brigid K Byrd
(74) *Attorney, Agent, or Firm* — Eversheds Sutherland (US) LLP

(57) ABSTRACT

A surgical instrument has at least one tool unit including at least one first tool element, at least one second tool element, and at least one coupling element that is connected to the second tool element, the at least one coupling element and the second tool element being supported in such a way that they are together displaceable relative to the first tool element along at least one displacement axis, and has an actuation, which includes at least one actuation element that is coupled with the coupling element in at least one first position of the coupling element relative to the second tool element, wherein for the purpose of releasing the actuation element, the coupling element is transferred from the first position into at least one second position relative to the second tool element.

17 Claims, 6 Drawing Sheets

Figure 1:
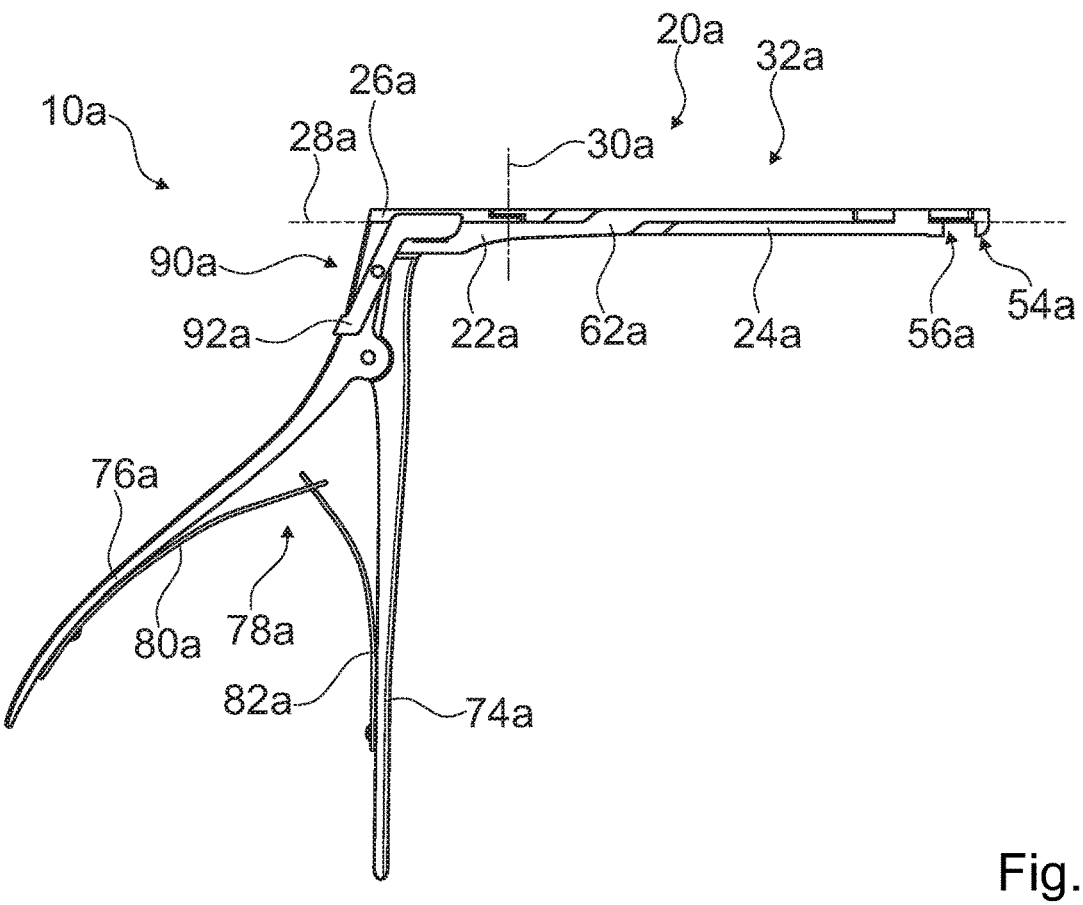

(51) Int. Cl.
*A61B 17/16* (2006.01)
*A61B 17/00* (2006.01)

(52) U.S. Cl.
CPC .......... *A61B 2017/00398* (2013.01); *A61B 2017/00464* (2013.01); *A61B 2017/00477* (2013.01); *A61B 2017/2926* (2013.01); *A61B 2017/2946* (2013.01); *A61B 2090/0813* (2016.02)

(58) Field of Classification Search
CPC ...... A61B 2017/292; A61B 2017/2947; A61B 2018/00601
See application file for complete search history.

(56) References Cited

U.S. PATENT DOCUMENTS

| | | | |
|---|---|---|---|
| 8,206,408 B2* | 6/2012 | Rebstock | A61B 17/1611 606/167 |
| 8,801,714 B1* | 8/2014 | Bodor | A61B 17/1611 606/83 |
| 2006/0189995 A1* | 8/2006 | Lancial | A61B 17/1611 606/83 |
| 2009/0209998 A1* | 8/2009 | Widmann | A61B 17/1611 606/207 |
| 2017/0086858 A1* | 3/2017 | Schreider | A61B 17/1611 |

* cited by examiner

SURGICAL INSTRUMENT

STATE OF THE ART

The invention relates to a surgical element according to the preamble of claim 1 and to a method for disassembly of a surgical instrument according to the preamble of claim 15.

Document DE 10 2006 012 754 A1 discloses a surgical instrument according to the preamble of claim 1, which is at least partially disassemblable for the purpose of cleaning the instrument.

The objective of the invention is in particular to provide a generic device with improved characteristics regarding disassemblability, in particular for cleaning purposes. The objective is achieved according to the invention by the features of claims 1 and 15, while advantageous implementations and further developments of the invention may be gathered from the subclaims.

DISCLOSURE OF THE INVENTION

The invention is based on a surgical instrument with at least one tool unit comprising at least one first tool element, at least one second tool element and at least one coupling element that is connected to the second tool element, the at least one coupling element and the second tool element being supported in such a way that they are together displaceable relative to the first tool element along at least one displacement axis, and with an actuation unit, which is preferably operable manually and which comprises at least one actuation element that is coupled with the coupling element in at least one first position of the coupling element relative to the second tool element.

It is proposed that the coupling element releases the actuation element in at least one second position relative to the second tool element.

By a "surgical instrument" is in particular an instrument to be understood which is configured for cutting and/or shearing and/or clamping and/or gripping invasive processes and/or for other invasive processes known to someone skilled in the art, in particular in a human body. In particular, the surgical instrument may be implemented as a bone punch and/or as an ear forceps and/or as a medical tissue punch and/or as a grasping forceps and/or as a preparation forceps and/or as a speculum and/or as retractors and/or may be used, in particular in the field of otorhinolaryngology, to carry out biopsies and/or the like. By a "tool unit" is in particular a unit to be understood which is, in at least one operating state, in direct contact with at least one object that is to be processed, in particular human tissue.

By a "coupling element" is in particular an element to be understood which, in at least one operating state, connects a first element to at least one further element at least regarding a force impact. The term "supported displaceably" is herein in particular to define a support of a unit and/or of an element, wherein the unit and/or element have/has a freedom of motion along at least one axis of more than 2 mm, preferably more than 4 mm and particularly preferably more than 6 mm, in particular in a fashion decoupled from an elastic deformation of the unit and/or element. By a "displacement axis" is in particular an axis to be understood which is advantageously situated at least partly along a translational movement, in particular along a translational movement of the second tool element.

At least one first element being "connected" to at least one further element is in particular to mean that the first element is advantageously connected to the further element via at least one force-fit implementation and/or at least one form-fit implementation, e.g. by a riveting and/or a latch connection and/or a tongue-and-groove connection and/or a clamp connection and/or another connection that is deemed expedient by someone skilled in the art, and/or connected to the further element via substance-to-substance bond, e.g. by a welding process, a gluing process, an injection-molding process and/or any other process deemed expedient by someone skilled in the art, the connection preferably at least partially allowing a movement of the first element relative to the further element, wherein in particular at least one degree of freedom of the movement is restricted by the connection.

By an "actuation unit" is in particular a unit to be understood which is configured for an actuation of the tool unit by a user, in particular by a doctor and/or a doctor's assistant. By the actuation unit being operable "manually" is in particular to be understood that the actuation unit is actuated, in at least one operating state, by a user, in particular by the user's own force, advantageously by the force of a user's hand. Alternatively or additionally the actuation unit may be operated, in at least one operating state, at least partly autonomously, preferably via an active drive unit, e.g. a motor. Preferentially the actuation unit comprises a first handle element and at least one second handle element, which are in particular configured for manually operating the tool element and are for this purpose in particular graspable. Especially preferentially the first handle element is supported movably, in particular pivotably, relative to the second handle element. In particular, the first handle element is connected to the actuation element preferably in a fixed fashion, and particularly preferably in a one-part implementation. In particular, the actuation unit is at least partly connected to the second tool element. The second handle element is connected to the second tool element preferably in a fixed fashion, and particularly preferably in a one-part implementation.

"In a one-part implementation" is in particular to mean at least connected by substance-to-substance bond, e.g. by a welding process, a gluing process, an injection-molding process and/or by any other process deemed expedient by someone skilled in the art, and/or advantageously formed in one piece like, for example, by production from one cast and/or by production in a one-component or multi-component injection molding procedure and advantageously from a single blank.

Preferentially the coupling element comprises a recess, which is at least partly configured for an accommodation and/or guidance of the actuation element. The coupling element furthermore advantageously comprises a force transmission surface, which in particular contacts the actuation element directly, in particular for the purpose of a force transmission from the actuation unit to the tool unit. By the coupling element being "released" from the actuation element is in particular to be understood that in particular a contact between the coupling element and the actuation element has been released, wherein advantageously the coupling element and the second tool element, which is connected to the coupling element, are releasable from the actuation unit and/or from the first coupling element.

"Configured" is in particular to mean specifically designed and/or specifically equipped. By an object being configured for a certain function is in particular to be understood that the object fulfills and/or implements said certain function in at least one application state and/or operating state.

By an implementation according to the invention, improved characteristics regarding a disassemblability are achievable. In particular, it is advantageously possible, subsequently to usage in a cleaning process, to disassemble the surgical instrument into its principal individual parts and/or structural components quickly and easily. Moreover the actuation unit and/or the tool unit, preferably their surfaces, hollow spaces, lumina and/or openings, are reliably accessible by machine cleaning and/or manual cleaning. In this way advantageously a risk of infection, in particular within a living organism, is reducible. It is furthermore advantageously possible to quickly and efficiently assemble the first tool element and/or the actuation unit with the second tool element, in particular subsequently to cleaning. This advantageously allows increasing reliability and/or preferably patient safety, as a result of which in particular a risk of injury may be minimized for the patient.

It is also proposed that the coupling element is supported on the second tool element pivotably around at least one pivot axis. Preferentially, between the first position and the second position of the coupling element relative to the second tool element, there is a rotational angle of at least 5°, preferably at least 15° and especially advantageously 30°, and in particular maximally 90°, preferably maximally 75° and especially advantageously 45°. This advantageously allows facilitating a secure, simple and quick unlocking.

Advantageously the pivot axis is oriented at least substantially perpendicularly to the displacement axis. The term "at least substantially perpendicularly" is herein in particular to define an orientation of a direction relative to a reference direction, wherein the direction and the reference direction, in particular when viewed in a plane, include an angle of 90°, the angle having a maximum deviation of in particular less than 8°, advantageously less than 5° and particularly advantageously less than 2°. In this way advantageous haptics is achievable. Moreover a secure locking may be provided, which is in particular not self-releasing.

In a further implementation it is proposed that the pivot axis is oriented at least substantially parallel to a main extension plane of the actuation unit. A "main extension plane" of an object is in particular to mean a plane which is parallel to a largest side surface of a smallest imaginary rectangular cuboid just still entirely enclosing the object, and which in particular extends through the center of the rectangular cuboid. "At least substantially parallel" is herein in particular to mean an orientation of a direction relative to a reference direction, in particular in a plane, wherein the direction differs from the reference direction in particular by less than 8°, advantageously by less than 5° and especially advantageously by less than 2°. In particular, due to this the coupling element is pivotable sideways relative to the actuation unit. Advantageously the pivot axis is at least substantially parallel to a straight main extension line of the first handle element. By a "straight main extension line" of an object is herein in particular a straight line to be understood which extends parallel to a largest edge of a smallest imaginary rectangular cuboid just still enclosing the object. Alternatively the pivot axis may be arranged at least substantially perpendicularly to the main extension plane of the actuation unit, as a result of which in particular the coupling element is pivotable upwards relative to the actuation unit. In this way a locking of the tool unit may be provided which is particularly easy to operate as well as secure.

It is furthermore proposed that the tool unit comprises at least one slide bearing unit, which in its first position connects the second tool element to the first tool element and supports the second tool element on the first tool element in a slidable fashion. Preferentially the slide bearing unit comprises at least one first slide bearing element, which is connected, preferably integrally connected, to the first tool element, and comprises at least one corresponding second slide bearing element, which is connected, preferably integrally connected, to the second tool element, the slide bearing elements being embodied in particular in such a way that they slide on each other due to at least one form-fit implementation. In this way advantageously a stable and secure displacement of the second tool element relative to the first tool element is achievable.

Beyond this it is proposed that in the second position a support provided by the slide bearing unit is releasable and the second tool element is releasable from the first tool element. In particular, at least for the purpose of releasing the second tool element, the slide bearing unit comprises an opening and/or a recess, via which advantageously a bearing, at least a bearing of a slide bearing element, is releasable. In particular, a bearing is releasable by a displacement of the second tool element relative to the first tool element, in particular along the displacement axis. In this way it is advantageously possible to provide a stable tool unit, thus in particular allowing easy release.

It is advantageous that the second tool element is, in particular in the second position, releasable from the first tool element by a movement along the displacement axis. Preferably, to release the second tool element, the movement of the second tool element along the displacement axis is directed at least partly toward the actuation element. This advantageously allows further simplifying a release of the second tool element from the first tool element.

In an especially preferred implementation of the invention it is proposed that the slide bearing unit supports the coupling element in the first position in such a way that it is slidable on the first tool element. In particular, the slide bearing unit comprises a guide part, which is connected, in particular fixedly and preferably integrally connected, to the coupling element and is configured for a guidance of the coupling element on the first tool element. In particular, the guide part may be additionally configured for a stabilization of the second tool element. Preferentially the guide part is embodied as a tongue and is configured to engage in a groove of the slide bearing unit, wherein the groove is connected to the first tool element in particular fixedly, and preferably integrally. Preferably the groove is additionally configured to provide a guidance of the actuation element. In particular, the second tool element comprises an opening, which is in particular configured to release the guide part in a pivoting of the coupling element relative to the second tool element. This advantageously allows rendering a simple and flexible construction available.

It is further proposed that the surgical instrument comprises at least one locking unit, which locks the coupling element in the first position. Advantageously the locking unit at least partly prevents a release of the first tool element from the second tool element. Alternatively or additionally it is possible that the locking unit at least partly comprises a latch element, which may in particular be configured to latch the coupling element at least in the first position. In particular, the latch element is herein embodied at least partly as a nub and/or corner and/or contour, which is in particular fixedly, preferably integrally, connected to the coupling element and/or to the second tool element. In this way reliability may be increased, thus allowing to ensure a high level of patient safety.

In a particularly preferred implementation of the invention it is proposed that the locking unit comprises at least one locking element, which is supported pivotably relative to the tool unit. The term "supported pivotably" is herein in particular to define a support of a unit and/or of an element, wherein the unit and/or the element have/has, in particular in a fashion decoupled from an elastic deformation of the unit and/or the element, a freedom of movement around at least one axis by an angle that is greater than 10°, preferably greater than 40° and especially preferentially greater than 70°. This advantageously allows a locking to be improved further. Moreover an additional stabilization of the tool unit in the first position is achievable.

It is also proposed that the locking element at least partly prevents a pivoting of the coupling element relative to the second tool element. Especially preferably a pivoting is prevented in the first position. Alternatively or additionally the locking unit comprises at least one latch element which latches the coupling element in the second position. As a result, it is advantageously possible to further simplify an operability.

Furthermore it is proposed that the locking element is supported, in particular pivotably supported, on the first tool element. Preferably the locking element is connected to the first tool element by means of a rivet connection and/or a screw connection and/or a clamp connection and/or a latch connection and/or a further connection that is deemed expedient by someone skilled in the art. Moreover, in particular the pivot axis of the locking element is advantageously perpendicular to the pivot axis of the coupling element and/or perpendicular to the main extension plane of the actuation unit. Preferentially the locking element is only configured to carry out a rotational movement around the pivot axis. In this way a locking unit with an advantageously high level of stability and/or reliability may be made available.

In a further implementation of the invention it is proposed that the locking element is supported, in particular pivotably supported, on the coupling element. Advantageously the locking element is connected to the coupling element by a latch connection and/or by a riveting and/or by a clamp connection and/or by a further connection that is deemed expedient by someone skilled in the art. In particular, the locking element is in the first position displaceable along the displacement axis together with the coupling element and/or the second tool element. Advantageously a straight main extension line of the locking element is in the first position at least substantially parallel to the displacement axis. Preferably the locking element encompasses the actuation element at least partly. Furthermore, at least in the first position, in particular the pivot axis of the locking element is advantageously perpendicular to the pivot axis of the coupling element and/or perpendicular to the main extension plane of the actuation unit. Preferentially the locking element is configured to at least partially rotate around the pivot axis of the coupling element, advantageously together with the coupling element. This allows providing an advantageously user-friendly locking element.

Beyond this it is proposed that the slide bearing unit is embodied at least partly integrally with the locking unit. By the two units being embodied "at least partly integrally" with one another is in particular to be understood, in this context, that the two units share at least one element. Preferably the locking unit comprises at least one element which is also part of the slide bearing unit and in particular provides at least a slide bearing function. This advantageously allows improving stability. Moreover a number of structural components is reducible.

It is also proposed that the locking element provides at least one slide guide surface for the coupling element. In particular, the slide guide surface is embodied integrally with the locking element. Advantageously the slide guide surface is at least partly in direct contact with the first tool element, the second tool element and/or the coupling element. Preferentially the slide guide surface is configured to further stabilize an axial displacement along the displacement axis of the coupling element. This advantageously allows further increasing stability.

The invention is furthermore based on a method for disassembly of a surgical instrument with at least one tool unit comprising a first tool element, at least one second tool element and at least one coupling element that is connected to the second tool element, the at least one second tool element and the at least one coupling element being supported in such a way that they are together displaceable relative to the first tool element along at least one displacement axis, and with an actuation unit, which is preferably operable manually and which comprises at least one actuation element that is coupled with the coupling element, in at least one first position of the coupling element relative to the second tool element.

It is proposed that for the purpose of releasing the actuation element, the coupling element is transferred from the first position into at least one second position relative to the second tool element.

By the implementation according to the invention, improved characteristics are achievable regarding a disassemblability. It is in particular advantageously possible to quickly and easily disassemble the surgical instrument, subsequently to usage, for cleaning purposes, into its principal individual parts and/or structural components. Furthermore the actuation unit and/or the tool unit, preferably their surfaces, hollow spaces, lumina and/or openings, are advantageously reachable by machine cleaning and/or manual cleaning. This advantageously allows reducing an infection risk; in particular within a living organism. It is furthermore advantageously possible to assemble the first tool element and/or the actuation unit with the second tool element quickly and efficiently, in particular when cleaning has been carried out. This advantageously allows increasing reliability, as a result of which in particular an injury risk is minimizable for patients.

The surgical instrument is herein not to be restricted to the application and implementation described above. In particular, to fulfill a functionality described here, the surgical instrument may comprise a number of respective elements, structural components and units that differs from a number that is mentioned here.

DRAWINGS

Further advantages will become apparent from the following description of the drawings. In the drawings three exemplary embodiments of the invention are shown. The drawings, the description and the claims contain a plurality of features in combination. Someone skilled in the art will purposefully also consider the features separately and will find further expedient combinations.

Figure 2:
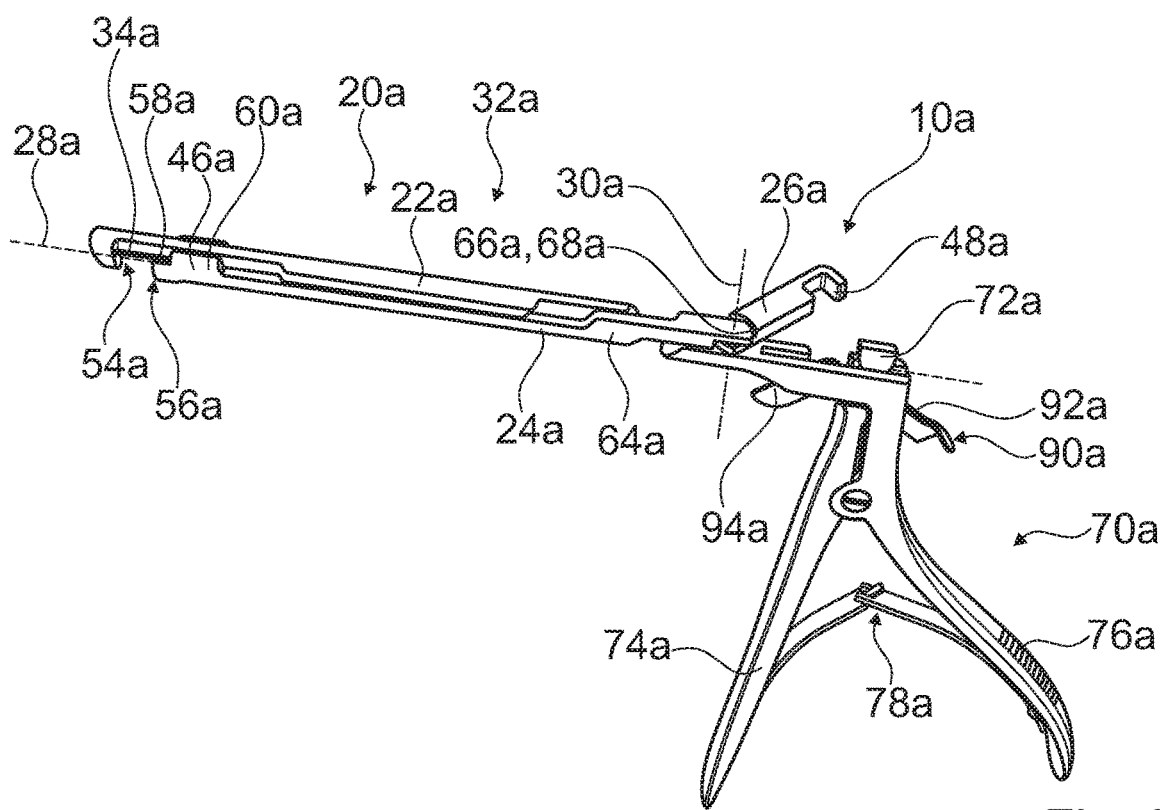
Figure 3:
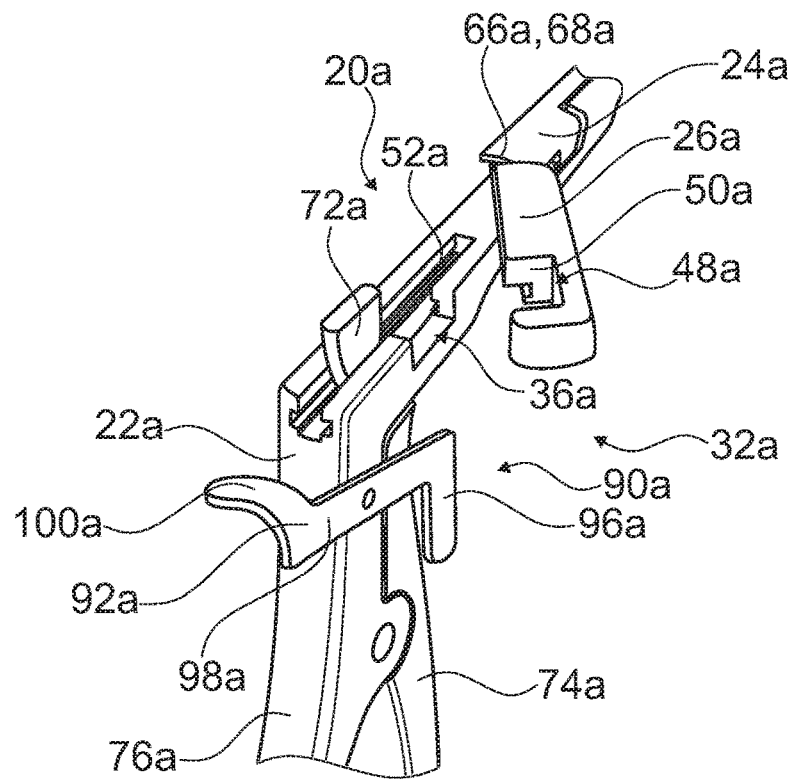
Figure 4:
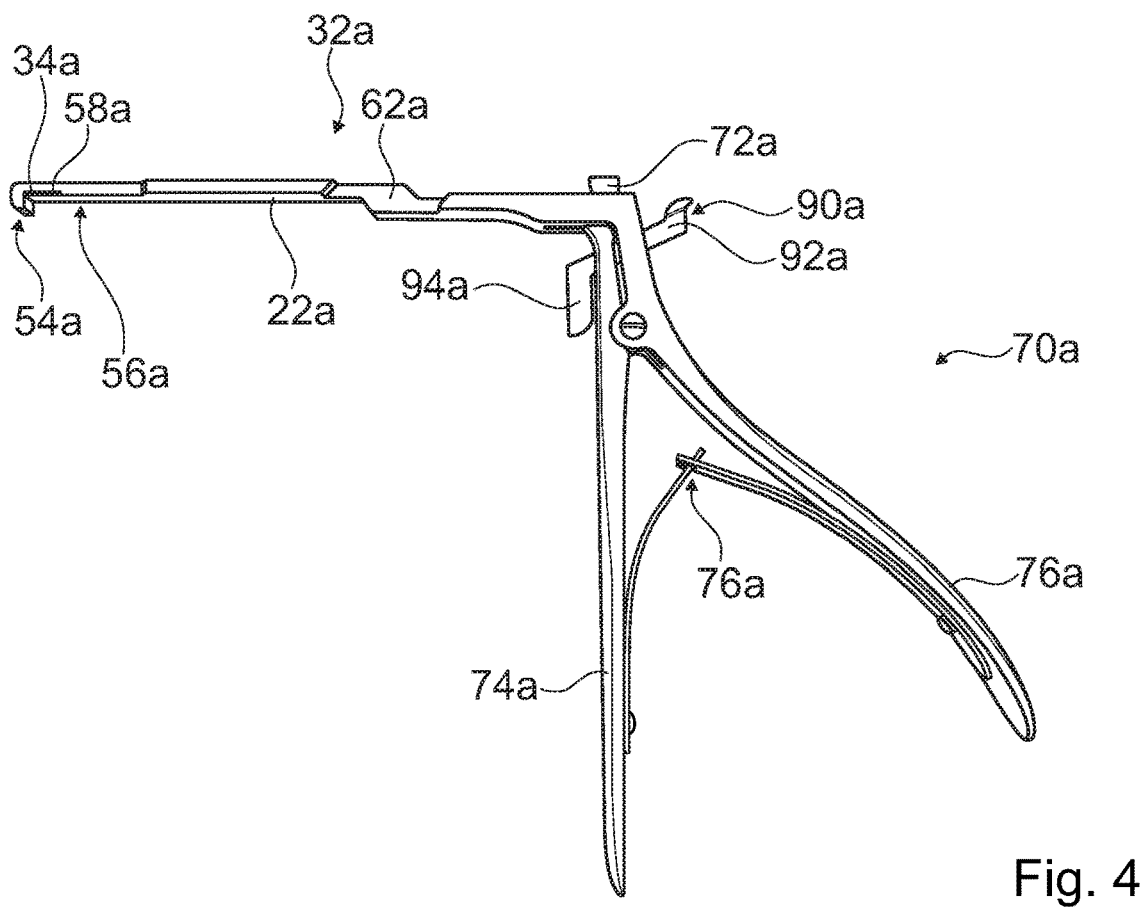
Figure 5:
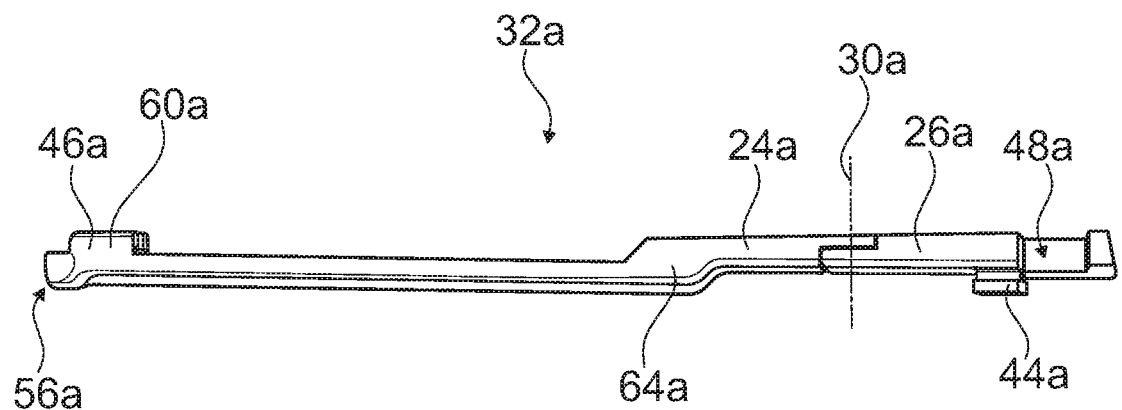
Figure 6:
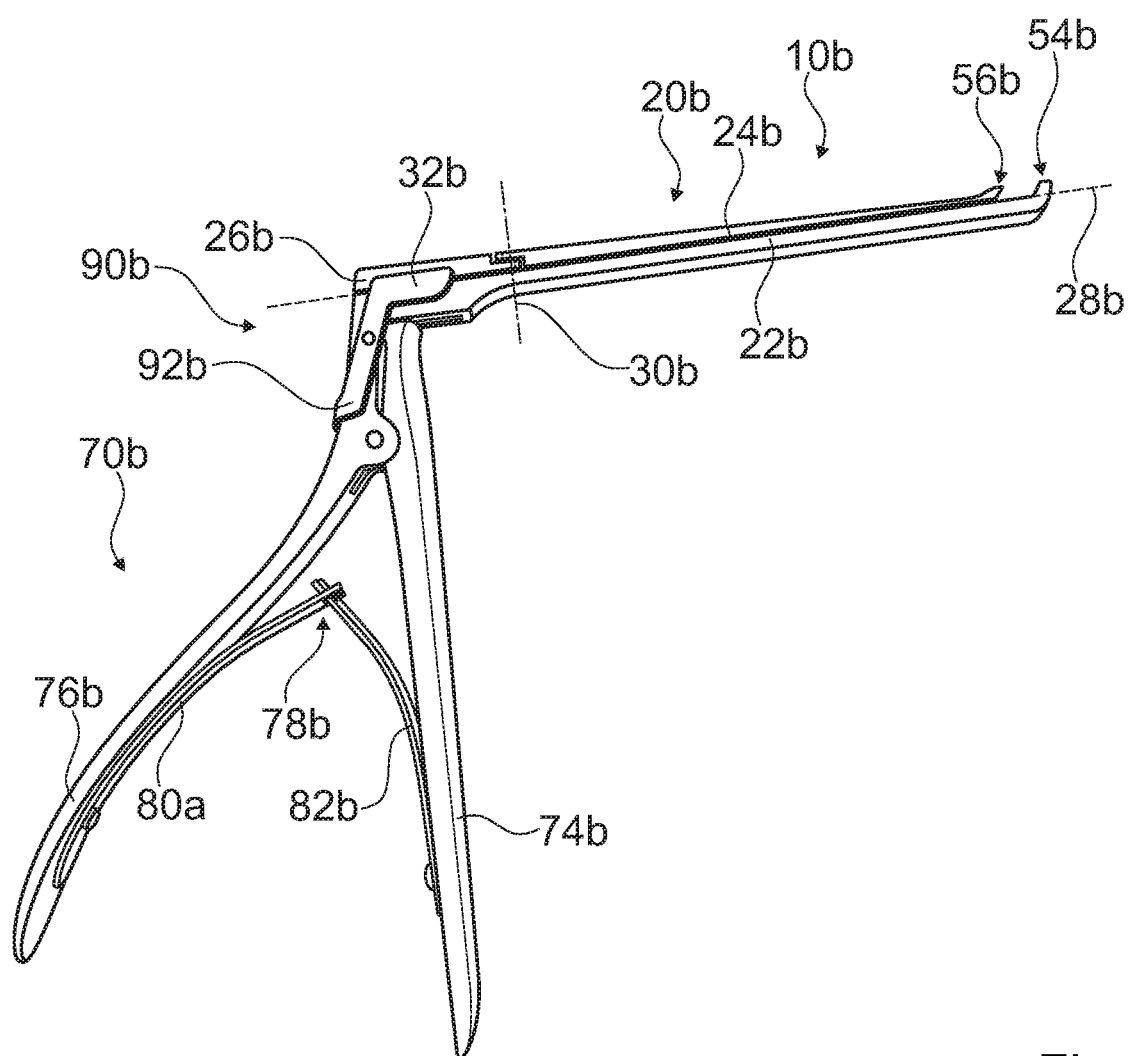
Figure 7:
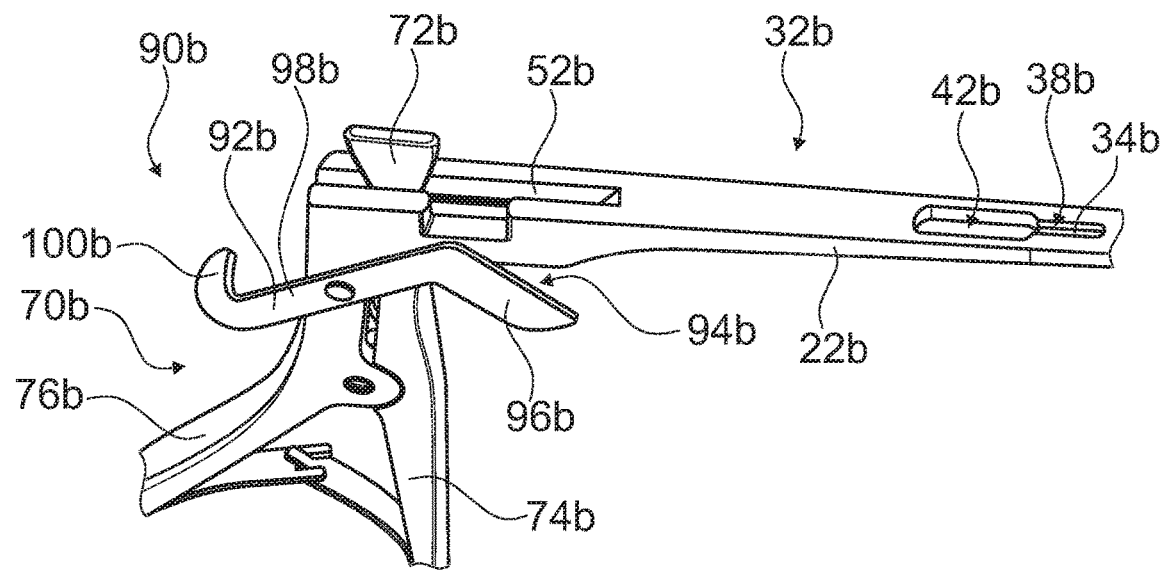
Figure 8:
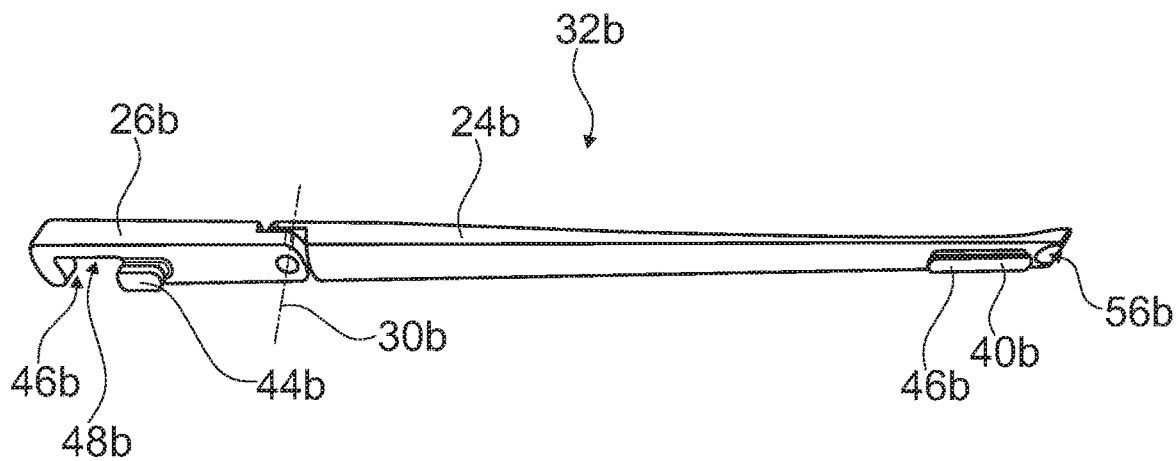
Figure 9:
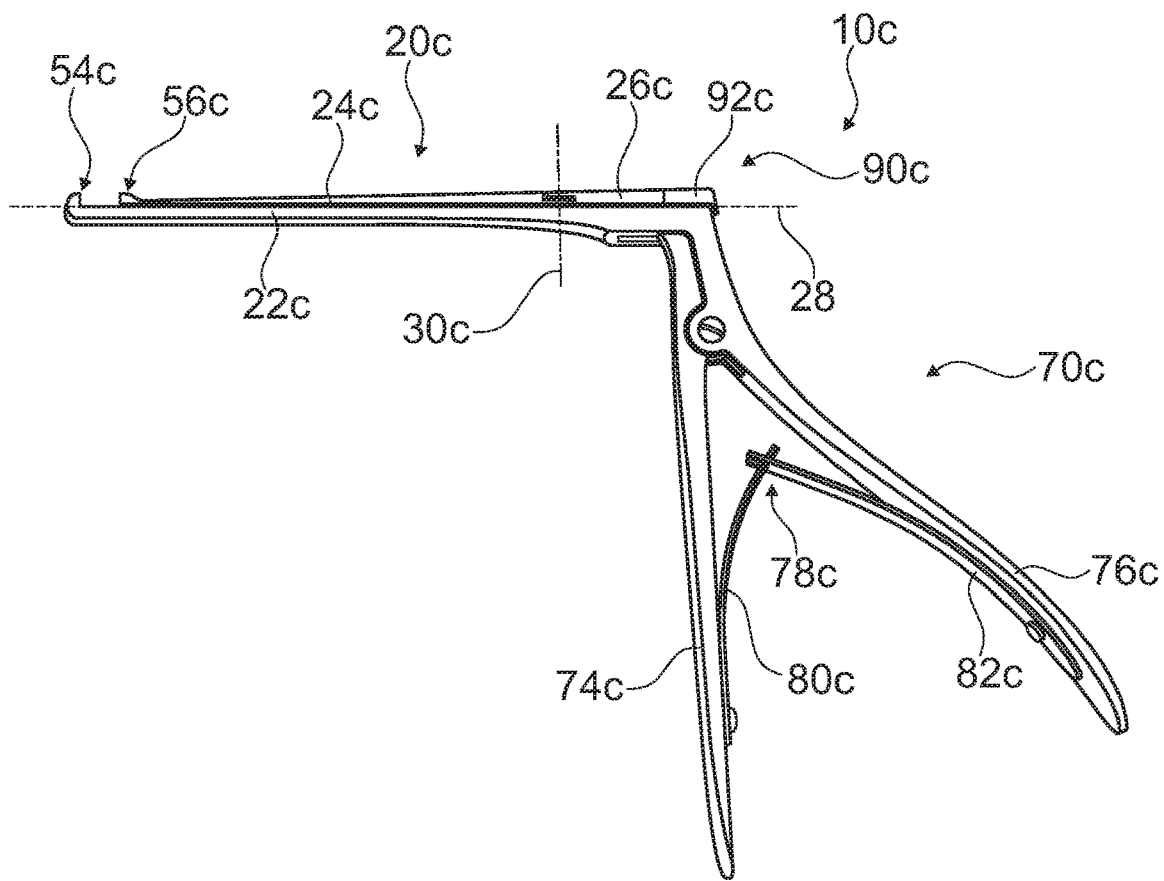
Figure 10:
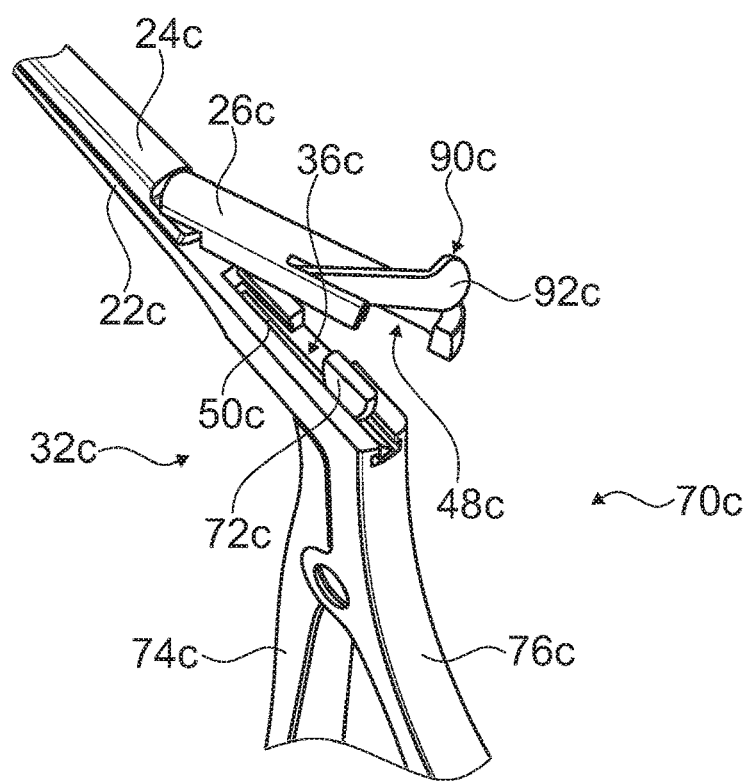
Figure 11:
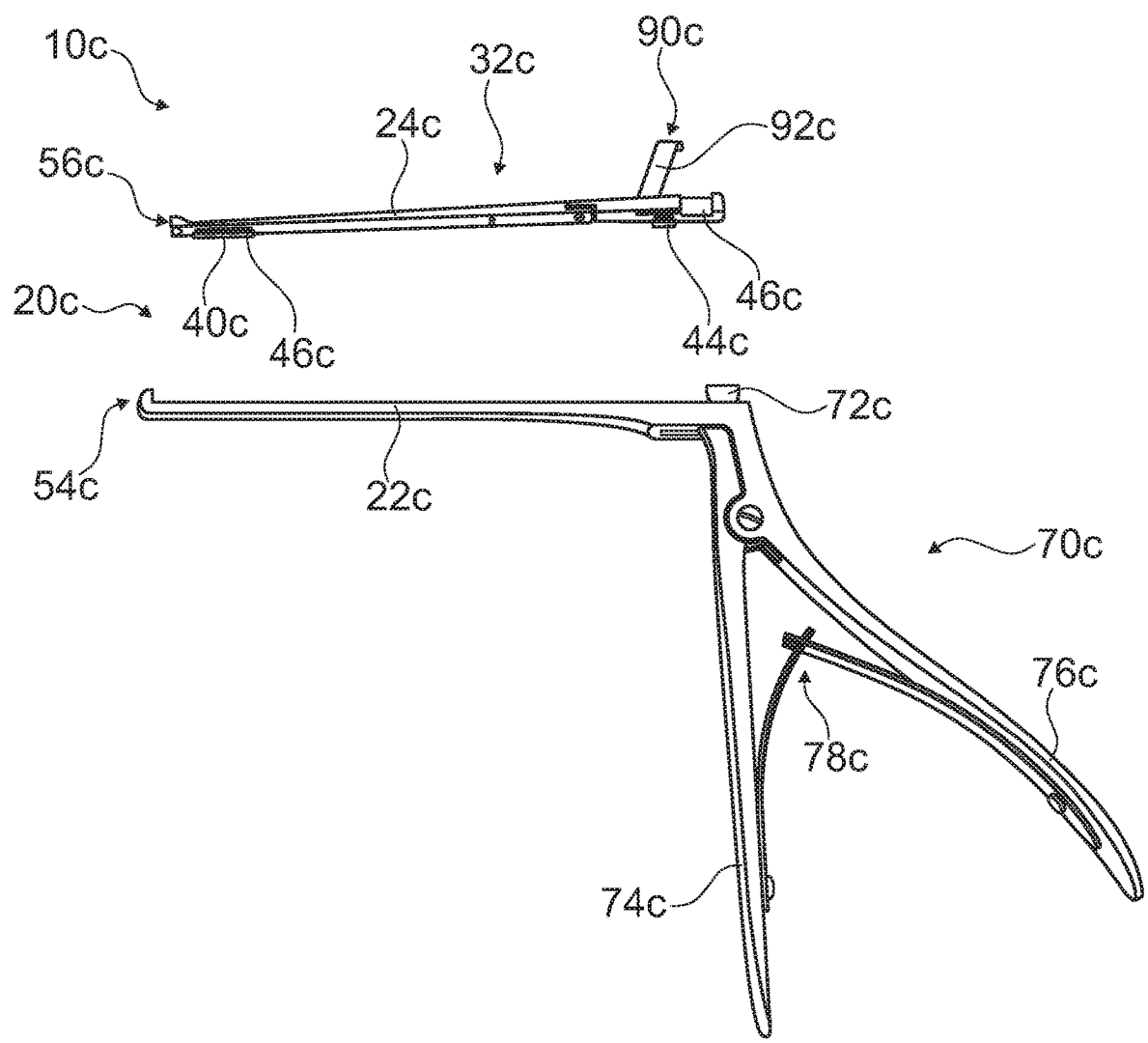

It is shown in:

FIG. 1 a surgical instrument comprising a tool unit with a first tool element, a second tool element and a coupling element, in an assembled state in which the coupling element is situated in a first position relative to the second tool element, FIG. 2 the surgical element in a second position of the coupling element relative to the second tool element, FIG. 3 a locking unit of the surgical instrument in the second position, in an unlocked state of the coupling element, FIG. 4 a portion of the surgical instrument, comprising the first tool element, FIG. 5 the second tool element and the coupling element in the first position, FIG. 6 an alternative surgical instrument, FIG. 7 a portion of the surgical instrument of FIG. 6, comprising a first tool element of a tool unit, FIG. 8 a second tool element and a coupling element of the tool unit of the surgical instrument of FIG. 6, in a first position of the coupling element relative to the second tool element, FIG. 9 a further surgical instrument, FIG. 10 the surgical instrument of FIG. 9 in a second position of a coupling element relative to a second tool element of a tool unit of the surgical instrument, and FIG. 11 the surgical instrument of FIG. 9 in a disassembled state.

DESCRIPTION OF THE EXEMPLARY EMBODIMENTS

FIG. 1 shows an isometric representation of a surgical instrument 10a in an assembled state. The surgical instrument 10a is configured for invasive processes in a human body. The surgical instrument 10a is embodied as a medical tissue punch.

The surgical instrument 10a comprises a tool unit 20a. The tool unit 20a comprises a first tool element 22a. The tool unit 20a comprises a second tool element 24a. The second tool element 24a is in the assembled state supported in such a way that it is translationally movable, relative to the first tool element 22a, along a displacement axis 28a. The tool unit 20a comprises a first cutter element 54a. The tool unit 20a comprises at least one second cutter element 56a. The first tool element 22a comprises the first cutter element 54a. The first tool element 22a is connected to the first cutter element 54a in a one-part implementation. The second tool element 24a comprises the second cutter element 56a. The second tool element 24a is connected to the second cutter element 56a in a one-part implementation. The second cutter element 56a is in the assembled state movable, together with the second tool element 24a, along the displacement axis 28a relative to the first cutter element 54a. The first cutter element 54a and the second cutter element 56a are embodied as punch-cutters. The first cutter element 54a is arranged at least substantially parallel to the second cutter element 56a. The first cutter element 54a has an at least substantially perpendicular arrangement relative to the first tool element 22a.

The surgical instrument 10a comprises a manually operable actuation unit 70a. The first cutter element 54a and the second cutter element 56a are open at least substantially toward the actuation unit 70a. The actuation unit 70a is configured for an actuation of the tool unit 20a. The actuation unit 70a is configured to displace the second tool element 24a relative to the first tool element 22a in the assembled state. The actuation unit 70a comprises a first handle element 74a. The actuation unit 70a comprises a second handle element 76a. The first handle element 74a and the second handle element 76a are arranged in such a way that they are rotatable to one another. The first handle element 74a and the second handle element 76a are connected via a bolt.

The first handle element 74a is connected to the second handle element 76a by a spring unit 78a of the actuation unit 70a. The spring unit 78a is configured to act counter to an actuation of the handle elements 74a, 76a and to guide them back into an original position. The spring unit 78a comprises a first spring element 80a. The spring unit 78a comprises a second spring element 82a. In a disassembly of the actuation unit 70a the spring unit 78a is separable at least partly into a first spring element 80a and a second spring element 82a. The first spring element 80a is connected to the second spring element 82a via a form-fit connection. The actuation unit 70a is connected to the first tool element 22a at least partially integrally. The second handle element 76a is connected to the first tool element 22a integrally (cf. FIGS. 2 and 4).

The actuation unit 70a comprises an actuation element 72a (cf. FIGS. 2, 3 and 4). The actuation element 72a is connected to the first handle element 74a in a one-part implementation. The actuation element 72a is configured for moving the second tool element 24a along the displacement axis 28a. The actuation element 72a is configured for moving a coupling element 26a of the tool unit 20a along the displacement axis 28a (cf. FIGS. 1, 2 and 3). The second tool element 24a is connected to the coupling element 26a. The second tool element 24a is riveted with the coupling element 26a. The coupling element 26a is in the assembled state supported in such a way that it is, together with the second tool element 24a, translationally movable on the displacement axis 28a relative to the first tool element 22a. The coupling element 26a is supported on the second tool element 24a in such a way that it is pivotable around at least one pivot axis 30a. The pivot axis 30a is implemented to be at least substantially perpendicular to the displacement axis 28a. The pivot axis 30a is arranged at least substantially in parallel to a main extension plane of the actuation unit 70a. The pivot axis 30a is at least substantially parallel to a straight main extension line of the second handle element 76a.

In at least one first position of the coupling element 26a relative to the second tool element 24a, the actuation element 72a is coupled with the coupling element 26a (cf. FIG. 1). In at least one second position relative to the second tool element 24a, the coupling element 26a releases the actuation element 72a (cf. FIGS. 2 and 3). The second tool element 24a is in this position releasable from the first tool element 22a. The coupling element 26a is in the second position pivoted outwards. The coupling element 26a is latchable in the second position by means of a latch element 66a. The second tool element 24a comprises the latch element 66a at least partly. The second tool element 24a provides at least one contour 68a. The contour 68a constitutes the latch element 66a. The contour 68a is configured to allow a latching of the coupling element 26a in the second position.

The coupling element 26a comprises a recess 48a. The recess 48a is configured to accommodate the actuation element 72a. The coupling element 26a comprises a force transmission surface 50a. The force transmission surface 50a is configured to establish a direct contact with the actuation element 72a. The force transmission surface 50a is configured for a direct force transmission from the actuation element 72a to the coupling element 26a.

The surgical instrument 10a comprises at least one locking unit 90a, which locks the coupling element 26a in the first position. The locking unit 90a comprises a locking element 92a. The locking element 92a is supported pivotably at least relative to the tool unit 20a. The locking element 92a is supported on the first tool element 22a (cf.

FIG. 3). The locking element 92a is riveted with the first tool element 22a. The locking element 92a provides at least one slide guide surface 94a for the coupling element 26a. The locking element 92a comprises at least one leg 96a, 98a, 100a. The locking element 92a comprises three legs 96a, 98a, 100a. A first leg 96a of the locking element 92a is at least partly implemented as the slide guide surface 94a. A second leg 98a is connected to the first tool element 22a. The first leg 96a and the second leg 98a include an angle between 90° and 120°. A third leg 100a is arranged at least partly perpendicularly to the first leg 96a. A main extension plane of the third leg 100a is at least partly perpendicular to the main extension plane of the actuation unit 70a. The third leg 100a is configured for stabilizing the locking element 92a in a locked state (cf. FIG. 3).

The tool unit 20a comprises at least one slide bearing unit 32a. The slide bearing unit 32a is configured to connect, in the first position, the second tool element 24a to the first tool element 22a. Via the slide bearing unit 32a, the second tool element 24a is supported slidably on the first tool element 22a. The slide bearing unit 32a comprises at least one first slide bearing element 34a. The slide bearing unit 32a comprises at least one second slide bearing element 46a (cf. FIG. 2). The first slide bearing element 34a and the second slide bearing element 46a are implemented to at least partly correspond to each other. The slide bearing element 34a is configured, together with the corresponding second slide bearing element 46a, for a stabilization of the second tool element 24a relative to the first tool element 22a. The first slide bearing element 34a comprises at least one rail piece 58a. The rail piece 58a of the first slide bearing element 34a is connected to the first tool element 22a in a one-part implementation (cf. FIG. 4). The second slide bearing element 46a is embodied as a slide part 60a. The slide part 60a is in particular configured for sliding on the rail piece 58a (cf. FIG. 2). The slide bearing unit 32a comprises a further first slide bearing element 62a and a corresponding further second slide bearing element 64a. The further slide bearing elements 62a, 64a are embodied shaped as specific three-dimensional contours of the first tool element 22a and the second tool element 24a, which contours are adapted to each other. A geometric engagement of the tool elements 22a, 24a is at least partly established by the three-dimensional contours.

The slide bearing unit 32a is at least partly implemented integrally with the locking unit 90a. The slide bearing unit 32a is at least partly implemented integrally with the locking element 92a. The slide guide surface e 94a of the locking element 92a is also part of the slide bearing unit 32a.

In the second position of the coupling element 26a relative to the second tool element 24a, a support provided by the slide bearing unit 32a is releasable. The rail piece 58a of the slide bearing element 34a comprises a railless portion (cf. FIG. 4). The second tool element 24a is releasable from the first tool element 22a by a movement along the displacement axis 28a. The second tool element 24a is herein moved towards the actuation unit 70a. In a movement of the second tool element 24a relative to the first tool element 22a, the slide part 60a of the slide bearing element 46a is guided in the railless portion. A support of the slide bearing element 46a is released in the railless portion.

The slide bearing unit 32a supports the coupling element 26a in the first position in such a way that it is slidable on the first tool element 22a. The slide bearing unit 32a comprises a guide part 44a, which is connected to the coupling element 26a (cf. FIG. 5). The guide part 44a is configured for a stabilization of the coupling element 26a. The guide part 44a is configured for guiding the second tool element 24a. The guide part 44a implements a tongue 40a for a tongue-and-groove connection. The first tool element 22a comprises a groove 52a for an accommodation of the guide part 44a. The groove 52a is configured to allow a sliding of the guide part 44. The first tool element 22a comprises an opening 36a (cf. FIG. 3). The opening 36a is configured to at least partly release the guide part 44a in a pivoting of the coupling element 26a from the first position into the second position.

In a disassembly of the surgical instrument 10a, the coupling element 26a is transferred from the first position into the second position relative to the second tool element 24a for the purpose of releasing the actuation element 72a. In a first method step the locking element 92a is moved. The locking element 92a is herein rotated. The locking element 92a releases the coupling element 26a. In a second method step the coupling element 26a is moved around the pivot axis 30a. In a pivoting the guide part 44a is guided from the first position of the coupling element 26a into the second position of the coupling element 26a, out of the opening 36a. In a third method step the second tool element 24a is displaced relative to the first tool element 22a. The second tool element 24a is displaced at least substantially toward the actuation unit 70a. The second tool element 24a is displaced along the displacement axis 28a. A support of the slide bearing unit 32a is at least substantially released. In a fourth method step the second tool element 24a is released from the first tool element 22a.

For an assembly of the surgical instrument 10a, the second tool element 24a is in a first method step slid onto the first tool element 22a. The slide bearing unit 32a at least partially connects the first tool element 22a to the second tool element 24a. In a second method step the coupling element 26a is moved from the second position into the first position. The guide part 44a is guided through the opening 36a. In a third method step the locking element 92a is pivoted from the second position of the coupling element 26a back into the first position of the coupling element 26a. The locking element 92a prevents a pivoting of the coupling element 26a.

In FIGS. 6 to 11 two further exemplary embodiments of the invention are shown. The following descriptions and the drawings are substantially limited to the differences between the exemplary embodiments, wherein regarding identically designated structural components, in particular regarding structural components having the same reference numerals, principally the drawings and/or description of the other exemplary embodiments, in particular of FIGS. 1 to 5, may be referred to. To distinguish between the exemplary embodiments, the letter a has been added to the reference numerals of the exemplary embodiment of FIGS. 1 to 5. In the exemplary embodiments of FIGS. 6 to 11 the letter a has been substituted by the letters b and c.

In FIGS. 6 to 8 a further surgical instrument 10b is shown. The surgical instrument 10b substantially differs from the surgical instrument 10a by an opening direction of a tool unit 20b.

A second tool element 24b of the tool unit 20b is implemented at least substantially rod-shaped (cf. FIG. 8). The tool unit 20b comprises a first cutter element 54b. The tool unit 20b comprises a second cutter element 56b. The first cutter element 54b is embodied in a one-part implementation with a first tool element 22b of the tool unit 20b. The second cutter element 56b is embodied in a one-part implementation with the second tool element 24b. The first cutter element 54b and the second cutter element 56b delimit an opening. The opening is configured for guiding an object that is to be processed between the first cutter element 54b and the second cutter element 56b. The first cutter element 54b is arranged at least substantially parallel to the second cutter element 56b. The first cutter element 54b includes an angle between 110° and 130° with the first tool element 22b.

The tool unit 20b comprises a slide bearing unit 32b. The slide bearing unit 32b comprises at least one first slide bearing element 34b (cf. FIG. 7). The slide bearing unit 32b comprises at least one second slide bearing element 46b (cf. FIG. 8). The first slide bearing element 34b is embodied at least partly as a groove 38b. The second slide bearing element 46b is embodied at least partly as a tongue 40b. The first slide bearing element 34b and the second slide bearing element 46b provide a tongue-and-groove connection. The tongue-and-groove connection is configured to allow a sliding of the second tool element 24b relative to the first tool element 22b.

For the purpose of releasing the second tool element 24b from the first tool element 22b, the slide bearing unit 32b comprises a further groove 42b. The further groove 42b is configured for releasing the second slide bearing element 46b. The further groove 42b is configured for releasing the tongue-and-groove connection. The further groove 42b directly follows the groove 38b. The further groove 42b is wider than the groove 38b by at least 30%. When the second tool element 24b is slid back relative to the first tool element 22b, the tongue 40b is arranged in the further groove 42b. The further groove 42b releases a support of the first side bearing element 34b relative to the second slide bearing element 46b.

In FIGS. 9 to 11 a further surgical instrument 10c is shown.

The surgical instrument 10c comprises a locking unit 90c with a locking element 92c. The locking element 92c is supported on a coupling element 26c of a tool unit 20c (cf. FIG. 10). The locking element 92c is riveted with the coupling element 26c. In a second position of the coupling element 26c relative to a second tool element 24c of the tool unit 20c, the locking element 92c is supported movably along a displacement axis 28c. A straight main extension line of the locking element 92c is at least substantially parallel to the displacement axis 28c, at least in a first position of the coupling element 26c relative to the second tool element 24c. The locking element 92c at least partly encompasses an actuation element 72c of an actuation unit 70c. A pivot axis of the locking element 92c is oriented perpendicularly to a pivot axis 30c of the coupling element 26c. The pivot axis of the locking element 92c is in the first position perpendicular to a main extension plane of the actuation unit 70c. In a pivoting of the coupling element 26c around the pivot axis 30c from the first position of the coupling element 26c to the second position of the coupling element 26c, the locking element 92c at least partly moves as well.

The tool unit 20c comprises a first cutter element 54c. The tool unit 20c comprises a second cutter element 56c. The first cutter element 54c and the second cutter element 56c are oriented in the same way as in the second exemplary embodiment shown in FIGS. 6 to 8. In a further exemplary embodiment, which is not shown, a first cutter element and a second cutter element are oriented in the same way as in the first exemplary embodiment shown in FIGS. 1 to 5.

We claim:

1. A surgical instrument with at least one tool unit comprising at least one first tool element, at least one second tool element and at least one coupling element that is connected to the second tool element, the at least one coupling element and the second tool element being supported in such a way that they are together displaceable relative to the first tool element along at least one displacement axis, and with an actuation unit, which comprises at least one actuation element that is coupled with the coupling element in at least one first position of the coupling element relative to the second tool element, wherein the coupling element releases the actuation element in at least one second position relative to the second tool element, and wherein the coupling element is in the at least one second position pivoted laterally outwards about at least one pivot axis that is perpendicular to the second tool element while the second tool element remains in place.

2. The surgical instrument according to claim 1, wherein the coupling element is supported on the second tool element pivotably around the at least one pivot axis.

3. The surgical instrument according to claim 2, wherein the pivot axis is oriented at least substantially perpendicularly to the displacement axis.

4. The surgical instrument according to claim 2, wherein the pivot axis is oriented at least substantially parallel to a main extension plane of the actuation unit.

5. The surgical instrument according to claim 1, wherein the tool unit comprises at least one slide bearing unit, which in its first position connects the second tool element to the first tool element and supports the second tool element on the first tool element in a slidable fashion.

6. The surgical instrument according to claim 5, wherein in the second position a support provided by the slide bearing unit is releasable and the second tool element is releasable from the first tool element.

7. The surgical instrument according to claim 6, wherein the second tool element is releasable from the first tool element by a movement along the displacement axis.

8. The surgical instrument according to claim 5, wherein the slide bearing unit supports the coupling element in the first position in such a way that it is slidable on the first tool element.

9. The surgical instrument according to claim 5, wherein the slide bearing unit is embodied at least partly integrally with a locking unit.

10. The surgical instrument according to claim 1, comprising at least one locking unit, which locks the coupling element in the first position.

11. The surgical instrument according to claim 10, wherein the locking unit comprises at least one locking element, which is supported pivotably relative to the tool unit.

12. The surgical instrument according to claim 11, wherein the locking element is supported on the first tool element.

13. The surgical instrument according to claim 11, wherein the locking element is supported on the coupling element.

14. The surgical instrument according to claim 11, wherein the locking element provides at least one slide guide surface for the coupling element.

15. The surgical instrument according to claim 10, wherein a slide bearing unit is embodied at least partly integrally with the locking unit.

16. A method for disassembly of a surgical instrument, in particular according to claim 1, wherein, for the purpose of releasing the actuation element, the coupling element is transferred from the first position into the at least one second position relative to the second tool element.

17. The surgical instrument according to claim 1, wherein the second tool element provides at least one contour, which constitutes a latch element and is configured to allow a latching of the coupling element in the second position.

* * * * *